United States Patent [19]

Chasalow

[11] Patent Number: 5,703,063
[45] Date of Patent: Dec. 30, 1997

[54] PHOSPHOCHOLINE DRUG DERIVATIVES

[75] Inventor: Fred L Chasalow, Glen Cove, N.Y.

[73] Assignee: Amur Research Corp., Belmont, Calif.

[21] Appl. No.: 748,025

[22] Filed: Nov. 12, 1996

Related U.S. Application Data

[63] Continuation of Ser. No. 348,355, Nov. 30, 1994, abandoned.

[51] Int. Cl.$^6$ ............................................. A61K 31/685
[52] U.S. Cl. ................................................ 514/78; 514/77
[58] Field of Search .................................... 514/77, 78

[56] References Cited

U.S. PATENT DOCUMENTS

| | | | |
|---|---|---|---|
| 4,552,869 | 11/1985 | Lautenschlager et al. | 514/77 |
| 4,891,208 | 1/1990 | Janoffe et al. | 424/1.1 |
| 4,897,385 | 1/1990 | Wissner et al. | 514/77 |
| 4,916,249 | 4/1990 | Brachwitz et al. | 558/169 |

FOREIGN PATENT DOCUMENTS 0 135 762   5/1984   European Pat. Off. ......... C07J 51/00

*Primary Examiner*—Theodore J. Criares
*Attorney, Agent, or Firm*—Darby & Darby

[57] ABSTRACT

Disclosed herein are methods for increasing the bioavailability of pharmaceutical agents by conjugation to phosphocholine. Also disclosed are phosphocholine-derivatized steroids, peptides and other biologically active agents and pharmaceutical formulations comprising these compounds.

10 Claims, No Drawings

PHOSPHOCHOLINE DRUG DERIVATIVES

This is a continuation of application Ser. No. 08/348,355, filed Nov. 30, 1994, now abandoned.

FIELD OF THE INVENTION

This invention pertains to methods and compositions for increasing the bioavailability of bioactive agents by conjugating them to phosphocholine.

BACKGROUND OF THE INVENTION

Conventional means for delivering pharmaceutical and therapeutic agents to mammals often are severely limited by chemical and physical barriers to uptake, as well as by susceptibility of administered agents to rapid metabolic inactivation following uptake. Oral delivery of many biologically-active agents would be the route of choice if not for the extreme pH of the stomach, the action of proteolytic and other digestive enzymes in the intestine, and the impermeability of gastrointestinal membranes to the active ingredient.

Methods for orally administering vulnerable pharmacological agents have relied on co-administration of adjuvants (e.g. resorcinols and non-ionic surfactants such as polyoxyethylene oleyl ether and n-hexadecyl polyethylene ether) to artificially increase the permeability of the intestinal walls; co-administration of enzymatic inhibitors (e.g. pancreatic trypsin inhibitor, diisopropylfluorophosphate (DFP) and trasylol) to avoid enzymatic degradation; and encapsulation of the active agent in liposomes or other delivery vehicles.

Irrespective of the mode of administration of many therapeutic compounds, once they gain access to body tissues or fluids they are then subject to rapid inactivation in the liver, termed the "first-pass effect." Orally administered compounds in particular are rapidly delivered to the liver via the portal circulation. Many compounds are acted upon by mixed-function oxidases, Phase I enzymes and other liver enzymes to produce inactive glucuronides, hippurates, glycyl and acetyl derivatives, which are rapidly excreted by the kidney.

There is thus a need in the art for methods and compositions to enable potential therapeutic agents to be rapidly absorbed in the intestine and avoid first-pass inactivation in the liver.

SUMMARY OF THE INVENTION

It has now been unexpectedly discovered that conjugation of many biologically active agents to phosphocholine via a phosphodiester bond will significantly enhance the bioactivity and/or the bioavailability of such agents.

In one aspect, the present invention provides a method for increasing the bioavailability of a pharmaceutical agent, comprising the steps of conjugating said agent to one or more phosphocholine moieties, and recovering said biologically active agent conjugated to phosphocholine.

In another aspect, the present invention provides a pharmaceutical formulation for treating a mammal suffering from hyposteroidism comprising a phosphocholine-conjugated active agent selected from the group consisting of testosterone, estradiol and etiocholanolone and a pharmaceutically-acceptable carrier or diluent.

In a further aspect, the present invention provides a composition of matter comprising a phosphocholine derivative of estradiol.

In a still further aspect, the present invention provides a composition of matter comprising a phosphocholine derivative of testosterone.

In yet another aspect, the present invention provides a pharmaceutical formulation for treating a mammal suffering from osteoporosis comprising a phosphocholine derivative of estradiol and a pharmaceutically acceptable carrier or diluents.

In yet another aspect, the present invention provides a pharmaceutical formulation for treating a mammal suffering from asthma comprising a phosphocholine derivative of theophylline and a pharmaceutically acceptable carrier or diluents.

In yet another aspect, the present invention provides a composition of matter comprising a phosphocholine derivative of theophylline.

These and other aspects of the present invention will be apparent to those of ordinary skill in the art in light of the present description, claims and drawings.

DETAILED DESCRIPTION OF THE INVENTION

All patent applications, patents, and literature references cited in this specification are hereby incorporated by reference in their entirety. In case of inconsistencies, the present description, including definitions, will prevail.

Definitions

"Phosphocholine-conjugated" or "phosphocholine-derivatized" defined herein as covalently bonded to a phosphocholine moiety via a phosphodiester linkage.

"Significantly enhanced bioactivity" in terms of the phosphocholine conjugated drugs of the present invention is defined herein as no less than 5 to 10-fold increased biological activity as compared to the unconjugated parent compound when administered by the same route.

The present invention is directed to increasing the bioavailability of pharmaceutically active agents, specifically by conjugation of such agents to a phosphocholine moiety via a phosphodiester bond.

Phosphocholine is a ubiquitous component of biological membranes, usually present in the form of phosphatidyl choline i.e., attached via a phosphodiester bond to diacyl glycerol. The two most common phosphocholine-containing molecules are lecithin and sphingomyelin. Both of these compounds can be hydrolyzed by phospholipase C at the phosphocholine phosphodiester bond to release diacyl glycerol and ceramides, respectively. Importantly, both lecithin and sphingomyelin, which are present in food, are absorbed in the gastrointestinal tract, incorporated into HDL- and LDL-cholesterol, and transported through the blood without significant first-pass metabolism in the liver.

In accordance with the present invention, conjugation of one or more phosphocholine moieties to lipophilic compounds will render them more hydrophilic, without abrogating their ability to traverse biological membranes. Without wishing to be bound by theory, it is contemplated that phosphocholine conjugation will, in most cases, mask the biological activity of the conjugated compounds. The phosphocholine conjugates will persist in conjugated form until they encounter enzymes such as phospholipase C, sphingomyelinase and non-specific esterases, which are present in the circulation and on target tissues. These enzymes will then remove the phosphocholine moiety and liberate the original compound with its biological activity in tact. In this manner, addition of phosphocholine is expected to protect compounds from first-pass inactivation in the liver and allow them to reach their sites of action in the blood or in peripheral tissues.

Pharmaceutical agents suitable for use in the present invention include, without limitation, lisophilic compounds that exhibit poor solubility in biological fluids, as well as compounds that are rapidly metabolized in the liver to hippurate, glucuronate, or other derivatives. Non-limiting examples of suitable compounds include those that are not presently utilized in pharmaceutical applications, in particular as orally administrable agents, because of problems with solubility, uptake, and metabolism. The only requirements for an agent to be used in the present invention are 1) the presence of a free alcohol functional group to which phosphocholine may be attached, and 2) the susceptibility of the resulting phosphodiester bond to cleavage by phospholipase C or other mammalian esterases.

Examples of pharmaceutical agents suitable for use in the present invention include without limitation steroids, catecholamines such as epinephrine or norepinephrine, prostaglandins such as prostaglandin E1 or E2, leukotrienes such as leukotriene B4, C4 or D4 and peptides. Peptides for use in the present invention are those which contain serine or threonine and preferably should not be longer than 10–15 amino acid residues in length such as Leutinizing Hormone Releasing Hormone (LHRH) (a 10 amino acid peptide) and its analoges. Preferred starting compounds or pharmacological agents include testosterone (available from Sigma, St. Louis, Mo.), etiocholanolone (Sigma), estradiol (Sigma), and dehydroepiandrosterone (Sigma). These steroids have only limited activity when administered orally.

According to the present invention, starting compounds may be converted to phosphocholine derivatives using any methods that are known in the art. In one preferred embodiment, phosphocholine (obtainable from Sigma Chemicals, St. Louis, Mo.) is reacted with a soluble carbodiimide, preferably 1-ethyl-3(3-dimethylaminopropyl)carbodiimide hydrochloride (EDAC, Sigma) in an active ester condensation reaction. This carbodiimide is preferred because it, similar to phosphocholine, is water-soluble. The active phosphoester intermediate is then reacted with a pharmaceutically active agent to yield the desired phosphocholine ester. The reaction is shown in Example 1 below. Phosphocholine in water is reacted with EDAC to yield the active ester. This is then reacted with e.g., testosterone or other biologically active starting compounds etc., to yield the final product

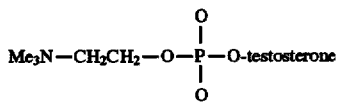

or other active esterification product. The product is expected to be essentially water-soluble and thus easily separated from the starting compound by conventional extraction and/or separation methods e.g. Flash Chromatography, Thin Layer Chromatography, High Performance Liquid Chromatography (HPLC) and the like, as is known to those of ordinary skill in the art.

Alternate methods for synthesis of phosphocholine derivatives include phosphorylation of the steroid, peptide, etc. with DPPP to give a phosphate ester, e.g., testosterone phosphate, which is coupled to choline using EDAC as the complexing agent.

The phosphocholine derivatized drugs of the present invention are expected to demonstrate enhanced biological activities and/or increased bioavailability. For example, etiocholanolone is metabolized by formation of the glucuronide in the liver of a mammal. After oral administration, about 99% of all free etiocholanolone is inactivated on each pass through the liver. When etiocholanolone is orally administered, it is absorbed in the gastrointestinal tract and transported via the portal circulation directly to the liver. Subsequently, only a fraction of a percent of the administered drug is biologically available for function. In contrast, phosphocholine-conjugated etiocholanolone may bind to form Low Density nipoprotein (LDL) and High Density Lipoprotein (HDL) cholesterol and is not expected to be degraded on first passage through the liver. In its phosphocholine-derivatized form, it is believed that about 80% of the etiocholanolone would not be metabolized at each pass. When the phosphocholine moiety is removed by an esterase, such as phospholipase C, sphingomyelinase, etc., then the parent compound will be available for binding and function in the target tissue. Glucuronidation would only occur on its return to the liver after removal of the phosphocholine moiety.

The phosphocholine-conjugated compounds of the present invention may be administered therapeutically by any route known in the art, e.g. orally, intravenously, intramuscularly, subcutaneously, by inhalation or in aerosol form, and topically. The present invention is particularly applicable to compounds that, in their unconjugated state, cannot be effectively administered by the oral route.

The phosphocholine-conjugated compounds of the present invention can be tested for efficacy as follows. A starting compound, and its phosphocholine derivative, may be administered by any of the above routes to a test animal e.g. rat, mouse, rabbit, guinea pig, and the like. Serum samples are then collected at increasing times after administration, and the levels of the starting and conjugated compound are assayed and compared. It will be understood by those skilled in the art that the method of assay will depend upon the starting compound. In the case of steroids or peptides, High-Performance Liquid Chromatography, Thin-Layer Chromatography, or immunoassay may be used to quantify serum levels. When the starting compounds are gonadal steroids, it may also be necessary to gonadectomize the test animals prior to drug administration, so as to suppress endogenous production of the test compound. Successful compounds are those whose serum level is increased significantly by administration of the phosphocholine derivative relative to administration of the starting compound or by their ability to reach therapeutically-significant serum levels when administered by an alternate route, e.g. orally.

In a second phase, the starting compound and its phosphocholine derivative will be administered to test animals, and the physiological effect of the compounds assayed over time. For example, for etiocholanolone and its phosphocholine derivative(s), rate of weight gain and changes in basal metabolic rate are measured. Estradiol and its phosphocholine derivative will be administered by garage to ovariectomized mice or rats and changes in uterine weight, breast development and estradiol blood levels will be measured. Testosterone and its phosphocholine derivative will be administered orally to castrate mice or rats and changes in seminal vesicles, prostate size, and levator ani muscle will be determined. Theophylline and its phosphocholine derivatives will be given orally to rats and the blood levels over the next 6 hours will be determined. From these tests, the degree to which the phosphocholine derivatives are more potent than the underivatized parent compound will be determined, i.e. the same response will be achieved with a smaller dose of the derivatized compound than the parent compound. This will be a measure of greater potency. Successful compounds are those whose functional endpoints are significantly lower for phosphocholine derivatives than for the starting compounds.

In a preferred embodiment of the present invention, testosterone is converted to testosterone-17-phosphocholine, and estradiol is converted to estradiol-3-phosphocholine or estradiol-17-phosphocholine. In like manner, theophylline is converted to theophylline phosphocholine. These compounds will frequently be given as replacement therapy for various hormone deficiencies and as pharmacological therapies in other cases. Theophylline is given to treat asthma, estradiol is administered to treat osteoporosis, etiocholanolone is given as a haemapoetic agent, to promote weight loss and to reduce diabetic blood sugar levels. These derivatives could also be used to provide enhanced levels of epinephrine.

The present invention also provides pharmaceutical formulations and dosage forms comprising the phosphocholine-derivatized drugs of the present invention. The pharmaceutical formulations of the present invention may also include, as optional ingredients, pharmaceutically acceptable vehicles, carriers, diluents, solubilizing or emulsifying agents, and salts of the type well known to those of ordinary skill in the art.

The phosphocholine-derivatized drugs of the present invention can be incorporated into pharmaceutical formulations to be used to treat mammals. Pharmaceutical formulations comprising the phosphocholine-conjugated drugs of the present invention as at least one of the active ingredients, would in addition optionally comprise pharmaceutically-acceptable carriers, diluents, fillers, salts and other materials well-known in the art depending upon the dosage form utilized. For example, preferred parenteral dosage forms may comprise a sterile isotonic saline solution, 0.5N sodium chloride, 5% dextrose and the like. Methyl cellulose or carboxymethyl cellulose may be employed in oral dosage forms as suspending agents in buffered saline or in cyclodextran solutions to enhance solubility.

It will be appreciated that the unit content of active ingredient or ingredients contained in an individual dose or dosage form need not in itself constitute an effective amount for the various usages of the phosphocholine-derivatized drugs of the present invention since the necessary effective amount can be reached by administration of a plurality of such dosage forms.

The following examples are intended to further illustrate the present invention without limiting it thereof.

EXAMPLE 1

SYNTHESIS OF PHOSPHOCHOLINE DERIVATIVES

Method 1

Phosphocholine (Sigma) (0.1 mol) is stirred in pyridine (Fisher, VWR) (100 ml) with 0.1 mol of morpholine (Sigma) and 0.1 mol of DDC (Sigma) for 6 hours under nitrogen or argon. At this point the reaction complex is stirred while 0.1 mol of steroid (etiocholanolone, estradiol, testosterone) are added. After stirring for an additional 3 hours the reaction mixture is diluted with 1 liter of ice water. The insoluble N,N' dicyclohexylurea is removed by filtration and the aqueous fraction is extracted with 4×0.5 volumes of ethyl acetate. The ethyl acetate is washed with saturated brine (0.1 vol) to remove the pyridine and dried over sodium sulfate. The solvent is removed by filtration and the product isolated by LH-20 column chromatography or by preparative HPLC.

Method 2

Phosphocholine (0.1 mol), steroid (0.1 mol) as above and DCC (0.12 mol) are stirred in 100 ml of pyridine (VWR) at 80° C. for 6 hours under nitrogen. The solution is diluted with 600 ml of water and processed as described above.

Method 3

Testosterone or other steroid, prostaglandin, etc. (0.1 mol) is reacted with $POCl_3$ in pyridine to yield the steroid sulfate. This product after drying in pyridine will then be reacted with 0.1 mol of EDAC at a rate just sufficient to maintain the pH at 7.0. The product is then purified as described above.

The compounds will then be analyzed by HPLC to determine purity of the reaction product, by NMR to verify the structure and by UV and IR spectra to determine their identity. Treatment with phosphatase (Lipase C) will then be used to cleave the diester to further establish the structural identity.

EXAMPLE 2

PHARMACOKINETICS OF TESTOSTERONE AND ITS PHOSPHOCHOLINE DERIVATIVE

The phosphocholine derivatives of testosterone (about 5 mg) is dissolved in 20 ml of buffered saline or in 20 ml of cyclodextran in saline and given orally to human volunteers. Alternatively, testosterone (5 mg) is suspended in a carboxymethyl cellulose suspending media, vortexed and then given orally. Blood samples will be taken at 30, 60, 120, 240, 360 and 720 minutes post-administration and collected in green top tubes. The blood samples are centrifuged and the plasma collected and stored as aliquots in microfuge tubes. The samples are then analyzed for testosterone in duplicate using a standard RIA kit (Diagnostics Products Corp., Tarzana, Calif.).

EXAMPLE 3

MEASUREMENT OF BIOACTIVITY OF PHOSPHOCHOLINE DERIVATIVES

The bioactivity of orally administered estradiol and estradiol phosphocholine will be determined in ovariectomized mice or rats. In addition, other animals will be briefly anesthetized and the steroid phosphocholine derivative or the free steroid will be administered intraperitoneally (IP). After 2 days the animals are sacrificed and the 4th and 9th inguinal breast tissue will be isolated. At the same time the uteri will be isolated and weighed. It is expected that the phosphocholine derivatized steroid will be more active than the parent compound when administered orally and by IP injection.

Estradiol and its phosphocholine derivative will also be administered by garage to ovariectomized mice or rats and changes in uterine weight, breast development and estradiol blood levels will be measured. Estradiol will be measured with an RIA kit from Diagnostics Products Corp. (Tarzana, Calif.).

Testosterone and its phosphocholine derivative will be administered orally to castrate male mice or rats and changes in seminal vesicles, prostate size, and levator ani muscle will be determined. Testosterone blood levels will also be measured by RIA using a kit from Diagnostics Products Corp. (Tarzana, Calif.). The compounds will also be characterized by UKV. Responses will also be measured after IP injection.

Theophylline and its phosphocholine derivatives will be given orally to rats and the blood levels of theophylline will be measured over the next 6 hours using an RIA kit (Diagnostics Products Corp., Tarzana, Calif.).

From these tests, the degree to which the phosphocholine derivatives are more potent than the underivatized parent hormone can be determined; i.e., the same response will be achieved with a smaller dose of the derivatized compound than the parent compound. This will be a measure of greater potency.

What is claimed is:

1. A pharmaceutical formulation comprising a phosphocholine-conjugated pharmaceutically active agent, said agent being selected from the group consisting of testosterone, estradiol, dehydroepiandrosterone, and etiocholanolone, and a pharmaceutically-acceptable carrier or diluent.

2. The pharmaceutical formulation of claim 1 wherein said agent is testosterone.

3. The pharmaceutical formulation of claim 1 wherein said agent is estradiol.

4. The pharmaceutical formulation of claim 1 wherein said agent is dehydroepiandrosterone.

5. The pharmaceutical formulation of claim 1 wherein said agent is etiocholanolone.

6. A method comprising administering the pharmaceutical formulation of claim 1 to an individual in need of said agent.

7. The method of claim 6 wherein said agent is testosterone.

8. The method of claim 6 wherein said agent is estradiol.

9. The method of claim 6 wherein said agent is dehydroepiandrosterone.

10. The method of claim 6 wherein said agent is etiocholanolone.

* * * * *